(12) United States Patent
Boebel et al.

(10) Patent No.: US 8,608,645 B2
(45) Date of Patent: Dec. 17, 2013

(54) STEREO-ENDOSCOPE WITH CAMERA CONNECTION

(75) Inventors: Manfred Boebel, Neulingen (DE);
Alexander Frank, Oberderdingen (DE);
Klaus-Peter Hipp, Bretten (DE);
Rudolf Heimberger, Oberderdingen (DE); Felix Bitrolf, Niefern-Öschelbronn (DE); Friedrich Haehnle, Bretten (DE); Carl-Sebastian Wagner, Bretten (DE); Stephan Prestel, Rheinstetten-Moersch (DE); Gerhard Fritz Buess, Windach (DE)

(73) Assignee: Richard Wolf GmbH, Knittlingen (DE)

( * ) Notice: Subject to any disclaimer, the term of this patent is extended or adjusted under 35 U.S.C. 154(b) by 404 days.

(21) Appl. No.: 12/468,170

(22) Filed: May 19, 2009

(65) Prior Publication Data
US 2009/0292170 A1  Nov. 26, 2009

(30) Foreign Application Priority Data
May 21, 2008   (DE) .......................... 10 2008 024 789

(51) Int. Cl.
*A61B 1/04*   (2006.01)
*A61B 1/06*   (2006.01)

(52) U.S. Cl.
USPC ........... 600/111; 600/160; 600/162; 600/166; 600/112

(58) Field of Classification Search
USPC ......... 600/109, 111, 112, 113, 117, 160, 162, 600/164, 165, 166; 348/45; 359/412–413, 359/376
See application file for complete search history.

(56) References Cited

U.S. PATENT DOCUMENTS

| | | | |
|---|---|---|---|
| 3,520,587 A | 7/1970 | Tasaki et al. | |
| 4,651,201 A | 3/1987 | Schoolman | |
| 4,834,518 A * | 5/1989 | Barber | 359/375 |
| 5,222,482 A | 6/1993 | Clark | |
| 5,385,138 A * | 1/1995 | Berry | 600/166 |
| 5,880,884 A | 3/1999 | Hauptli | |
| 5,969,859 A | 10/1999 | Afsenius | |
| 2001/0016679 A1 * | 8/2001 | Futatsugi et al. | 600/133 |
| 2004/0082836 A1 * | 4/2004 | Hino | 600/170 |
| 2008/0030848 A1 * | 2/2008 | Zimmer | 359/376 |

FOREIGN PATENT DOCUMENTS

GB    899922 A   6/1962

OTHER PUBLICATIONS

German Office Action dated Aug. 11, 2011 in Application No. 10 2008 024 789.8.
Office Action issued Dec. 23, 2011 in GB Application No. 0908606.7.

* cited by examiner

*Primary Examiner* — John P Leubecker
*Assistant Examiner* — Arnaldo Torres Diaz
(74) *Attorney, Agent, or Firm* — Panitch Schwarze Belisario & Nadel LLP

(57) ABSTRACT

A stereo-endoscope is provided having a hollow shank with two axially parallel optical channels, which channels run through the hollow shank and respectively form at least a section of an image path to respective oculars of a binocular observation device arranged on the proximal end of the hollow shank. Moreover, the stereo-endoscope includes a camera connection, and one of the optical channels also forms at least one section of an image path to the camera connection.

10 Claims, 8 Drawing Sheets

STEREO-ENDOSCOPE WITH CAMERA CONNECTION

BACKGROUND OF THE INVENTION

Stereo-endoscopes permit the user a spatial impression of a subject under observation. For this, these endoscopes in their hollow shank comprise two optical channels, which are aligned parallel to one another and which are respectively optically connected to an ocular of a binocular observation device, and give a perspective impression of the object under observation.

In this regard, stereo-endoscopes are known, which are also designed for the documentation of the image information provided by the stereo-endoscope. Apart from the two optical channels connected to the oculars of the observation device, these endoscopes in their hollow shank comprise a further optical channel, which is aligned parallel thereto and which is optically connected to a camera connection for a camera of a documentation device.

Since the optical axis of the optical channel connected to the camera connection is spaced from the optical axes of the optical channels connected to the oculars, with the known stereo-endoscopes of this type, it inevitably occurs that the image information represented on the documentation device differs from that of the observation device.

BRIEF SUMMARY OF THE INVENTION

Against this background, it is an object of the invention to create a stereo-endoscope which is designed for the direct optical observation of an object by a binocular observation device, as well as for the documentation of the image information, wherein the differences between the image information represented in the observation device and the image information recorded in the documentation device are reduced or completely eliminated, compared to the previously known stereo-endoscopes of this type.

The stereo-endoscope according to the invention, preferably a medical stereo-endoscope, comprises a hollow shank with two optical channels which run axially parallel through the hollow shank and which respectively form at least one section of the image path in each case to one ocular of a binocular observation device arranged at the proximal end of the hollow shank. Furthermore, the stereo-endoscope comprises a camera connection, wherein one of the optical channels also forms at least one section of an image path to the camera connection.

Accordingly, with the stereo-endoscope according to the invention, no separate optical channel, which runs through the hollow shank and which is optically connected to the camera connection, is necessary. Instead, the image information which is transmitted through one of the optical channels to the observation device by this optical channel is simultaneously also transmitted to the camera connection, whereby a very large agreement of the image evident on the documentation device with the image evident on the observation device results. A further advantage of this design is the reduced manufacturing expense for the stereo-endoscope.

Since the invention renders the presence of a separate optical channel to the camera connection superfluous, it is also possible to increase the cross sections of the two optical channels arranged in the hollow shank, for increasing the image brightness while simultaneously retaining the previous diameter of the hollow shank. Here, the largest possible cross sections of the image channels may be achieved when, as envisaged with a preferred embodiment of the stereo-endoscope according to the invention, the longitudinal axes of the optical channels are arranged in a common plane with a longitudinal axis of the hollow shank. Thus, the longitudinal axes of the two optical channels lie in a common diameter plane of the hollow shank with the longitudinal axis of the hollow shank.

In order to be able to lead the image information recorded at the distal end of an optical channel to the observation device as well as also to the camera connection, the invention advantageously envisages a beam splitter, which is arranged at the proximal end connecting to a first of the two optical channels, and which connects this optical channel to an ocular as well as to the camera connection. That is, a splitter prism is arranged at the proximal end of the first optical channel, and leads one part of the light beams exiting at the proximal end of the first optical channel to a camera connection, and leads the second part of these light beams to the ocular.

The division of image information by the beam splitter leads to a brightness distribution corresponding to the splitter ratio, so that the brightness of the respective part image is correspondingly reduced compared to the light exiting from the optical channel. This leads to the fact that differently bright images are transmitted to the ocular which is optically connected to the first optical channel via the beam splitter, and to the ocular which is optically connected to the second optical channel, in whose image path no beam splitter is arranged. In order to prevent this non-uniform brightness distribution with the visual observation by the observation device, the invention preferably envisages arranging means reducing the image brightness on the proximal end of the second optical channel.

By this measure, one succeeds in having the part images observed through the two oculars with the same brightness, but the total brightness of the image is however reduced. However, this is not a problem, since the stereo-endoscope according to the invention permits the use of optical channels, which compared to the optical channels in stereo-endoscopes with a camera connection and which have been known until now, have a significantly greater light-leading cross section. Thus, in this manner, the brightness reduction, caused on the one hand by the beam splitter and on the other band by the means for reducing the image brightness, is compensated, and the image brightness corresponds to that of stereo-endoscopes known until now, with an equal image disk.

Suitably designed optical apertures may, for example, be used as means for reducing the image brightness. Preferably however, a glass component is arranged on the proximal end of the second optical channel, which comprises a coating reducing the image brightness.

According to a further advantageous embodiment of the invention, the image path leading from the first optical channel to the ocular, and the image path leading from the first optical channel to the camera connection are angled to one another. Here, the image path formed by the first optical channel branches on the exit side of the beam splitter into two separate image paths, which are angled to one another. This design permits the arrangement of the camera connection on the stereo-endoscope, in a manner such that it and the camera connected thereto do not inhibit the user of the stereo-endoscope on visual observation by the observation device, and an additional channel for the connecting camera may be done away with.

The beam splitter is preferably formed by a deflection prism. That is, a prism is provided at the proximal end of the first optical channel, which divides the light beams exiting from the first optical channel and thereby deflects the resulting part light beams, according to the angle between the image path leading to the ocular and the image path leading to the camera connection. Preferably, the deflection prism is designed as a pentaprism.

Basically, with the stereo-endoscope according to the invention, the optical axes of the image paths leading from the optical channels to the oculars may be flush with the optical axes of the optical channels. However, the handling of a stereo-endoscope which is designed in such a manner is difficult in some cases of application. For this reason, a design is preferred in which the image paths, which on the proximal end lead from the optical channels to the observation device, are angled to the optical channels,. Here, deflection prisms may be arranged between the optical channels arranged in the hollow shank and the image paths leading from these to the two oculars. These deflection prisms are typically designed such that they respectively deflect the incident light beams according to the angle between the optical channel and the image path which leads from this to the ocular.

For further improving the operational ability of the stereo-endoscope according to the invention, its observation device may advantageously comprise a stationary ocular and an ocular which is displaceable to this in the longitudinal (distance) direction. The observation device may be adapted to different facial physiognomies in this way.

Particularly advantageously, the observation device comprises a sleeve which is aligned normally to the longitudinal axes of the oculars, wherein the displaceable ocular is displaceably guided within the sleeve in a longitudinal slot in an almost play-free manner. The central axis of the sleeve and its longitudinal slot run parallel to the longitudinal direction of the viewing distance of the user.

Preferably, the displaceable ocular is releasably fastened on the observation device. This makes sense inasmuch as moisture may penetrate into the observation device, via the longitudinal slot formed on the sleeve, during the cleaning of the stereo-endoscope by autoclaving. The release of the displaceable ocular permits an improved drying of this ocular, as well as of the remaining optical system of the observation device which is optically connected thereto, after the autoclaving.

One advantageous embodiment envisages designing the optical systems of the stereo-endoscope to be closed in a gas-tight and fluid-tight manner, in order to generally prevent a penetration of the water vapor, arising on autoclaving, into the optical systems of the stereo-endoscope according to the invention. Here, the housing parts which surround these optical systems, to which belong also shank parts, such as the hollow shank accommodating the two optical channels, are designed in a manner such that no water vapor may penetrate into them. If such housing consists of several housing parts, these may, for example, be welded or soldered to one another in a gas-tight manner at their connection locations. Typically, also the end-windows forming the ends of the optical system are welded or soldered in the housing in a gastight manner.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
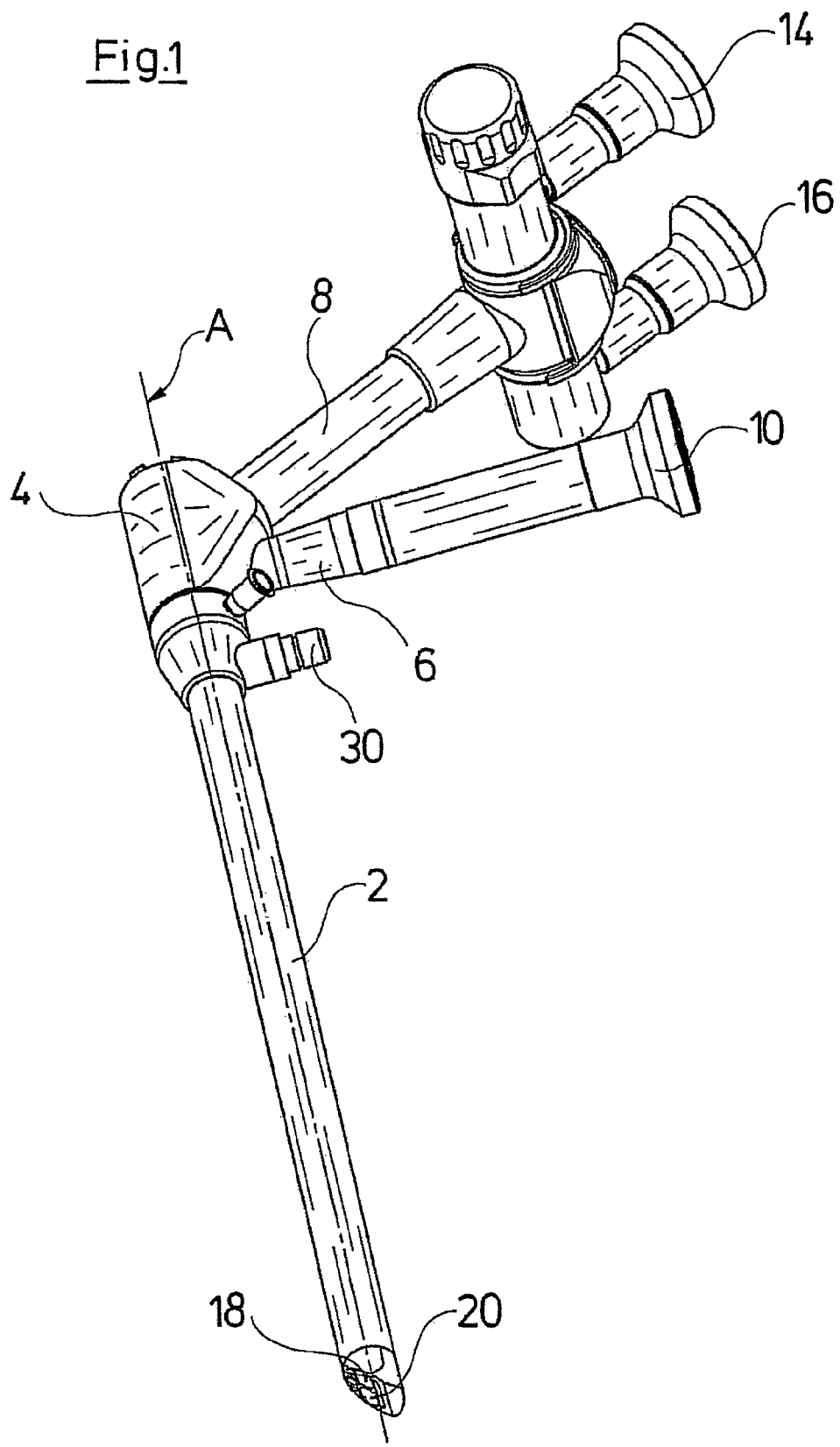
FIG. 1 is a perspective view of a stereo-endoscope according to an embodiment of the invention.
Figure 2:
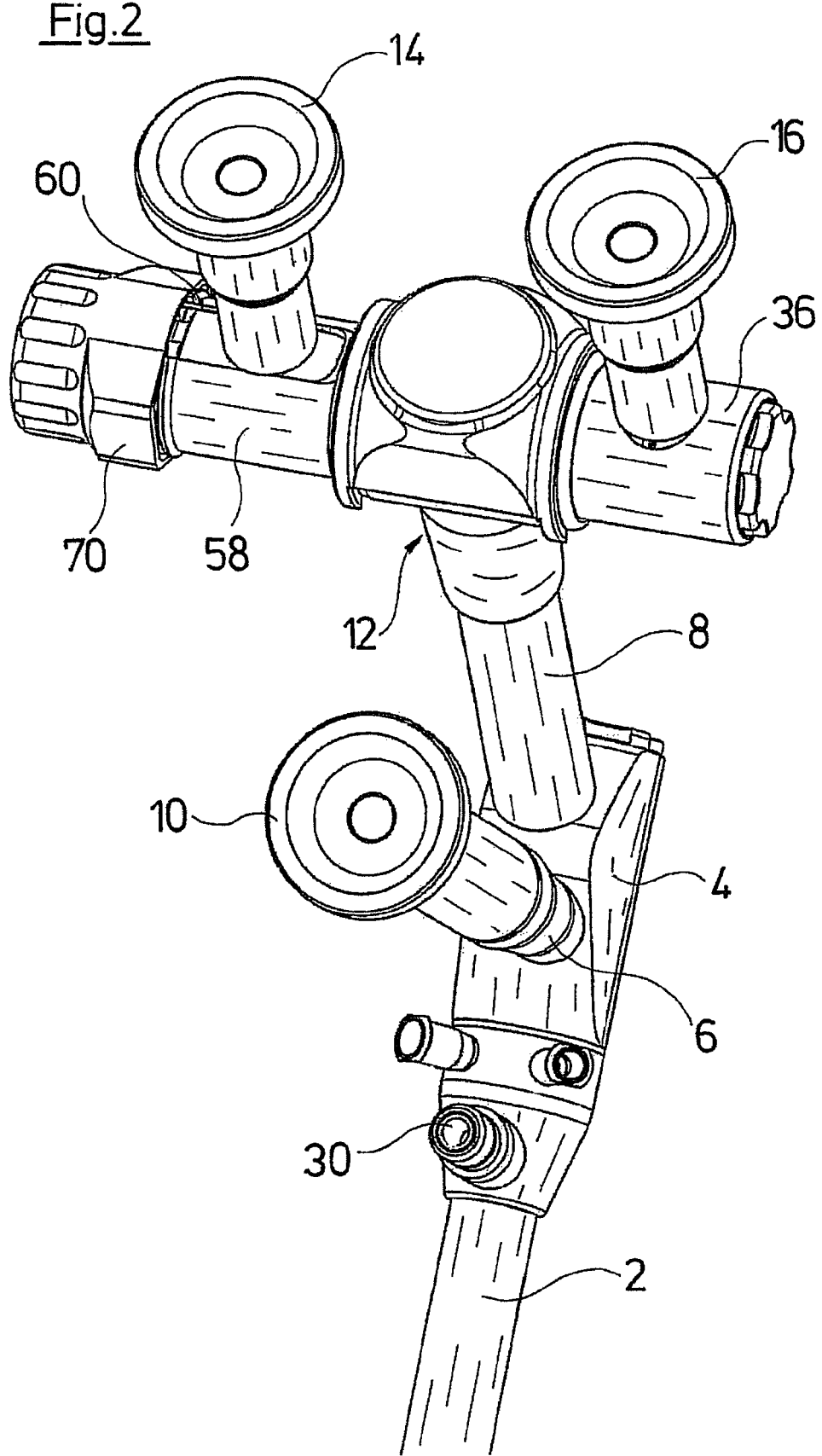
FIG. 2 is a perspective view of a proximal end region of the stereo-endoscope according to FIG. 1.

The stereo-endoscope according to one embodiment of the invention comprises on the distal end a hollow shank 2, to whose proximal end a housing 4 connects. A first hollow shank part 6 and a second hollow shank part 8 branch at the housing 4 at an angle to a longitudinal axis A of the hollow shank 2. The second hollow shank part 8 is arranged on the housing 4 on the proximal side of the first hollow shank part 6 and is angled in an oblique manner to the first hollow shank part 6 which is aligned normally to the longitudinal axis A of the hollow shank 2. A camera connection 10 is arranged at the proximal end of the hollow shank part 6, to which connection a camera (not shown) of a documentation device may be connected. A binocular observation device 12 with two oculars 14 and 16 is arranged on the proximal end of the hollow shank part 8.

Figure 4:
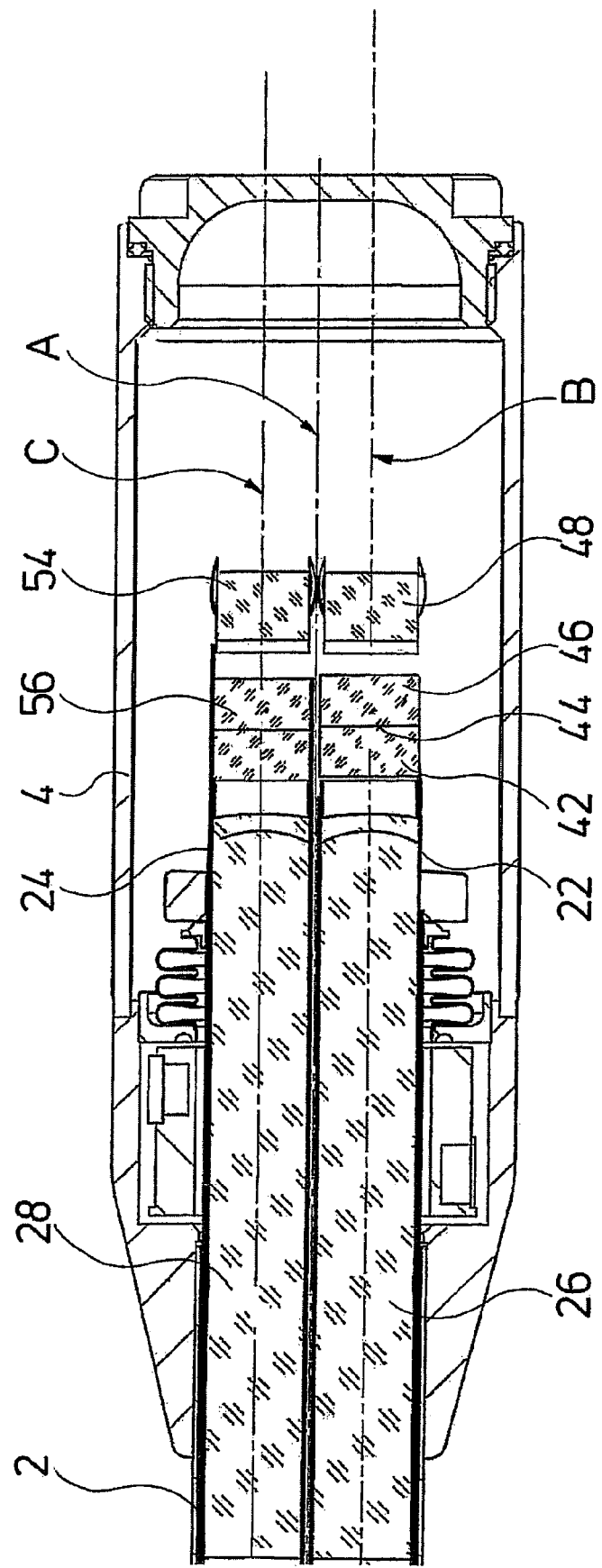
FIG. 4 is a sectional view of the region represented along a sectional plane IV-IV in FIG. 3.
Figure 5:
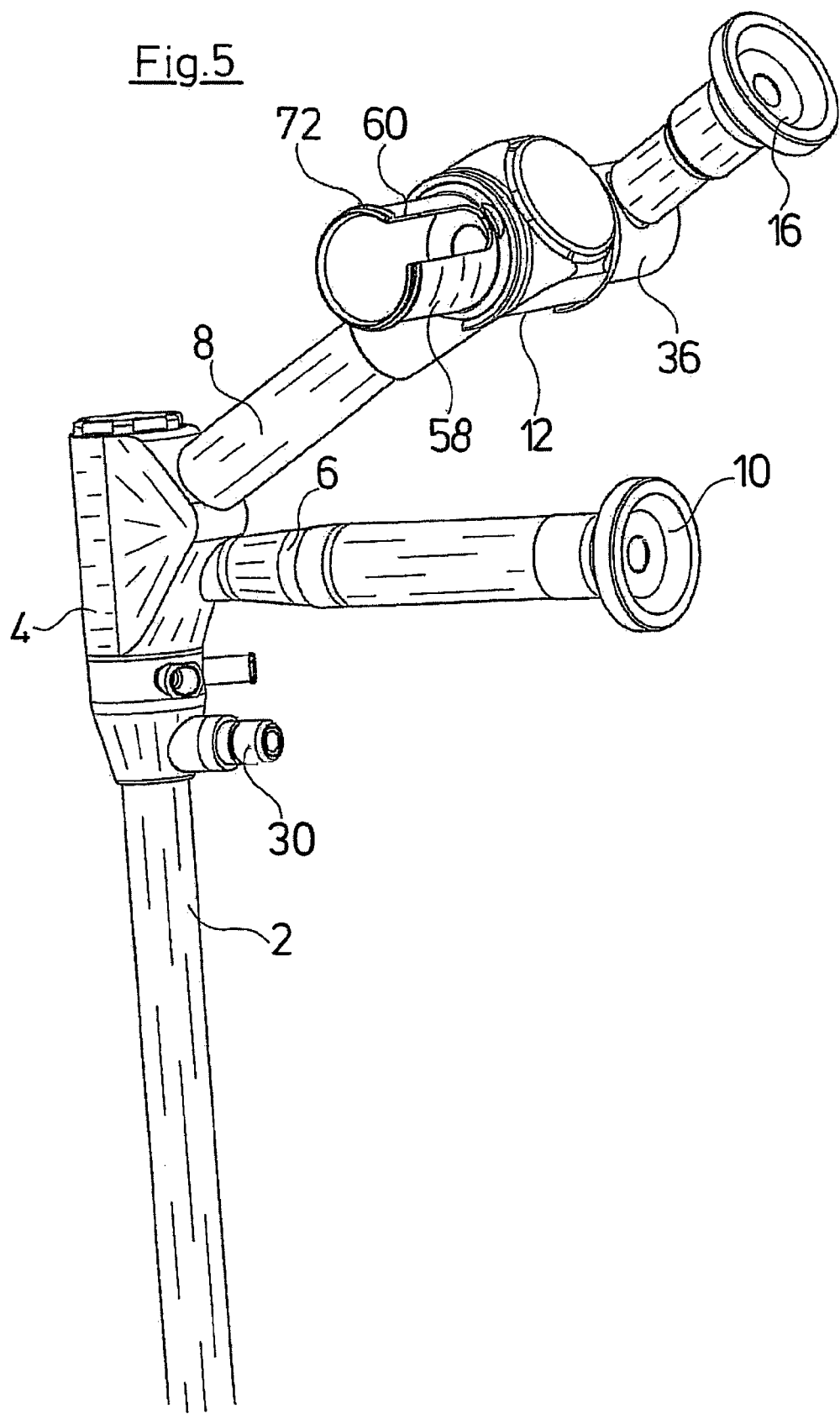
FIG. 5 is a perspective view of the proximal region of the stereo-endoscope according to FIG. 1, with a removed ocular.

Two transparent end-windows 18 and 20 are arranged at the distal end of the hollow shank 2, which is aligned obliquely to the longitudinal axis A of the hollow shank 2. These end-windows are soldered in a gas-tight manner into the distal end of the hollow shank 2, which is otherwise designed in a closed manner. The end-window 18 forms the distal end of a first optical channel 22 arranged in the hollow shank 2, while the end-window 20 forms the distal end of a second optical channel 24 arranged in the hollow shank 2. As shown in FIG. 4, these two optical channels 22 and 24 running out in the housing 4, are aligned parallel to one another in the hollow shank 2, wherein a longitudinal axis B of the first optical channel 22 and a longitudinal axis C of the second optical channel 24 lie in a common plane with the longitudinal axis A of the hollow shank 2. The cross sections of the optical channels 22 and 24, which are equally large, are dimensioned such that the sum of their outer diameters which are adjacent to one another, corresponds essentially to the complete inner diameter of the hollow shank 2, in order to be able to transmit as large a quantity of light as possible.

The optical channels 22 and 24 respectively form a section of an image path for transmitting an image of an object (not represented) situated on the exit side of the end-windows 18 and 22, to one of the respective oculars 14 and 16 of the observation device 12. For this purpose, common light-guiding optical components are arranged in the optical channels 22 and 24, of which components only one rod lens 26 arranged in the region of the proximal end of the first optical channel 22 and one rod lens 28 arranged in the region of the proximal end of the second optical channel 24 are represented in the FIGS. 3 and 4. A fiber-optic arranged in the hollow shank is connected in a light-guiding manner to a fiber-optic cable via a fiber optic cable connection 30 arranged on the housing 4 distally of the hollow shank 6, in order to be able to illuminate an object which is arranged for observation on the exit side of the end-windows 18 and 20.

Figure 3:
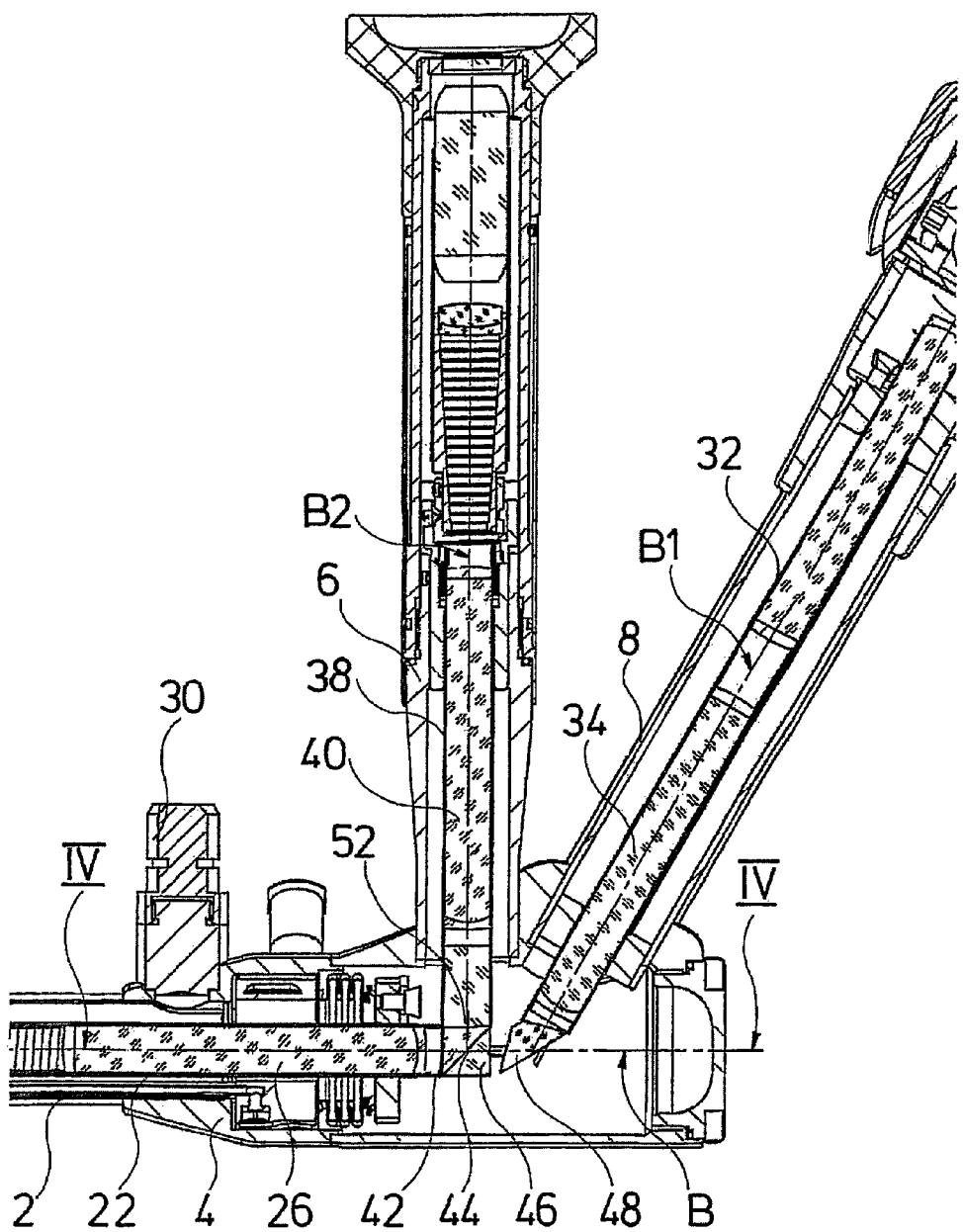
FIG. 3 is a sectional view of a region of the stereo-endoscope according to FIG. 1, in which, on the proximal end of an optical channel arranged in the hollow shank, one image path branches to a camera connection and one image path to an ocular.

Two optical channels, which are aligned parallel to one another, are arranged in the hollow shank part 8, of which only one optical channel 32 with a rod lens 34 on the entry side is represented in FIG. 3, and which respectively form a further part of the image path to one of the oculars 14 and 16. The optical channel 32, whose longitudinal axis B1 lies in a common plane with the longitudinal axis B of the first optical channel 22 of the hollow shank 2, forms a part of the image path from the housing 4 to the ocular 16 of the observation device 12, wherein the light exiting proximally of the optical channel 32 in a tubular component 36 adjacent the proximal end of the hollow shank part 8, is led further, in a manner known per se, via deflection prisms provided in the component 36, to the ocular 16 arranged in the component 36. In a corresponding manner, the second optical channel of the hollow shank part 8, which is not shown in the drawings, lies in a common plane with the longitudinal axis C of the second optical channel 24 of the hollow shank 2, wherein the light entering at the distal end of this optical channel is led in the manner described above to the ocular 14 arranged on the component 58.

The hollow shank part 6 also comprises an optical channel 38 with a rod lens 40 arranged therein, wherein the longitudinal axis B2 of the optical channel 38 lies in a common plane with the longitudinal axis B of the optical channel 22 of the hollow shank 2, and with the longitudinal axis of the optical channel 32 of the second hollow shank part 8.

A glass body in the form of a prism 42 is arranged in the housing 4 on the exit side of the optical channel 22 and on the entry side of the optical channel 32 in the hollow shank part 8, as well as on the entry side of the optical channel 38 in the hollow shank part 6. The prism 42 and a glass component 46 form a beam splitter, which is arranged in a manner such that it leads the image information exiting from the optical channel 22 to the image path in the form of the optical channel 38 to the camera connection 10, which image path is arranged in the hollow part 6, as well as to the optical channel 32, which is in the hollow shank part 8 and which forms a part of the image path to the ocular 16.

The prism 42 is arranged in a manner such that the light exiting from the optical channel 22 is first incident onto a partly transparent and partly reflecting prism surface 44. A part of the light flow exits from the prism 42 at this prism surface 44 and is led, via the glass component 46 arranged at the exit side of the prism surface 44, to a deflection prism 48 arranged at the entry side of the optical channel 32. There, it is deflected to the optical channel 32 and from there is led to the ocular 16. Apart from this, a further part of the light flow is deflected at the prism surface 44 to a prism surface 52, where it leaves the prism 42 into the optical channel 38 to the camera connection 10.

Since a brightness distribution of the image exiting at the optical channel 22 occurs at the exit side of the prism 42, a glass component 56 is arranged at the exit side of the optical channel 24 of the hollow shank 2 and at the entry side of the second optical channel of the hollow shank 8, which forms a part of the image path to the ocular 14 and in front of which a deflection prism 54 is arranged. This glass component 56 reduces the image brightness to the same extent as the prism 42 by a coating deposited on the glass component 56.

Figure 6:
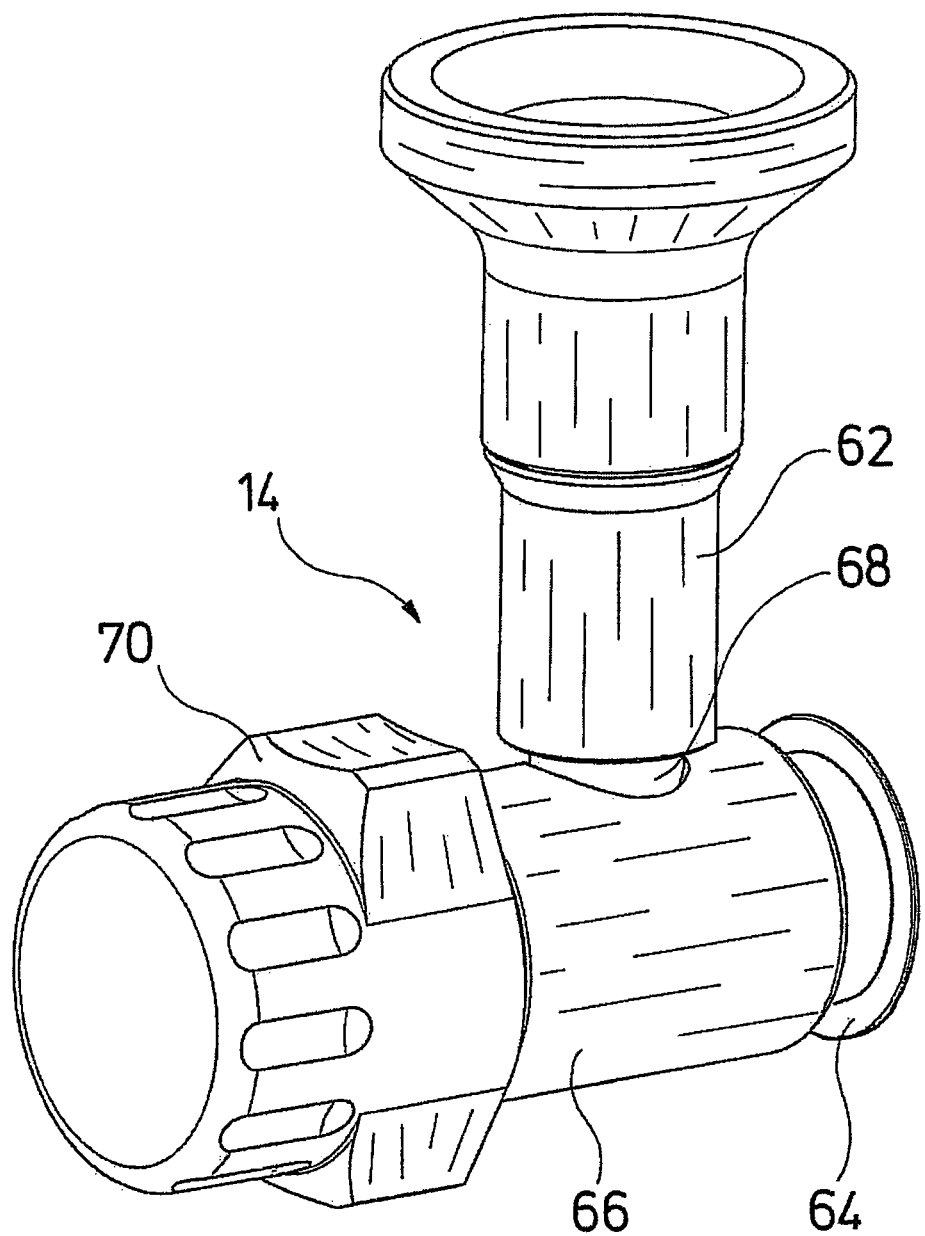
FIG. 6 is a perspective view of a removable ocular of the stereo-endoscope according to FIG. 1.
Figure 7:
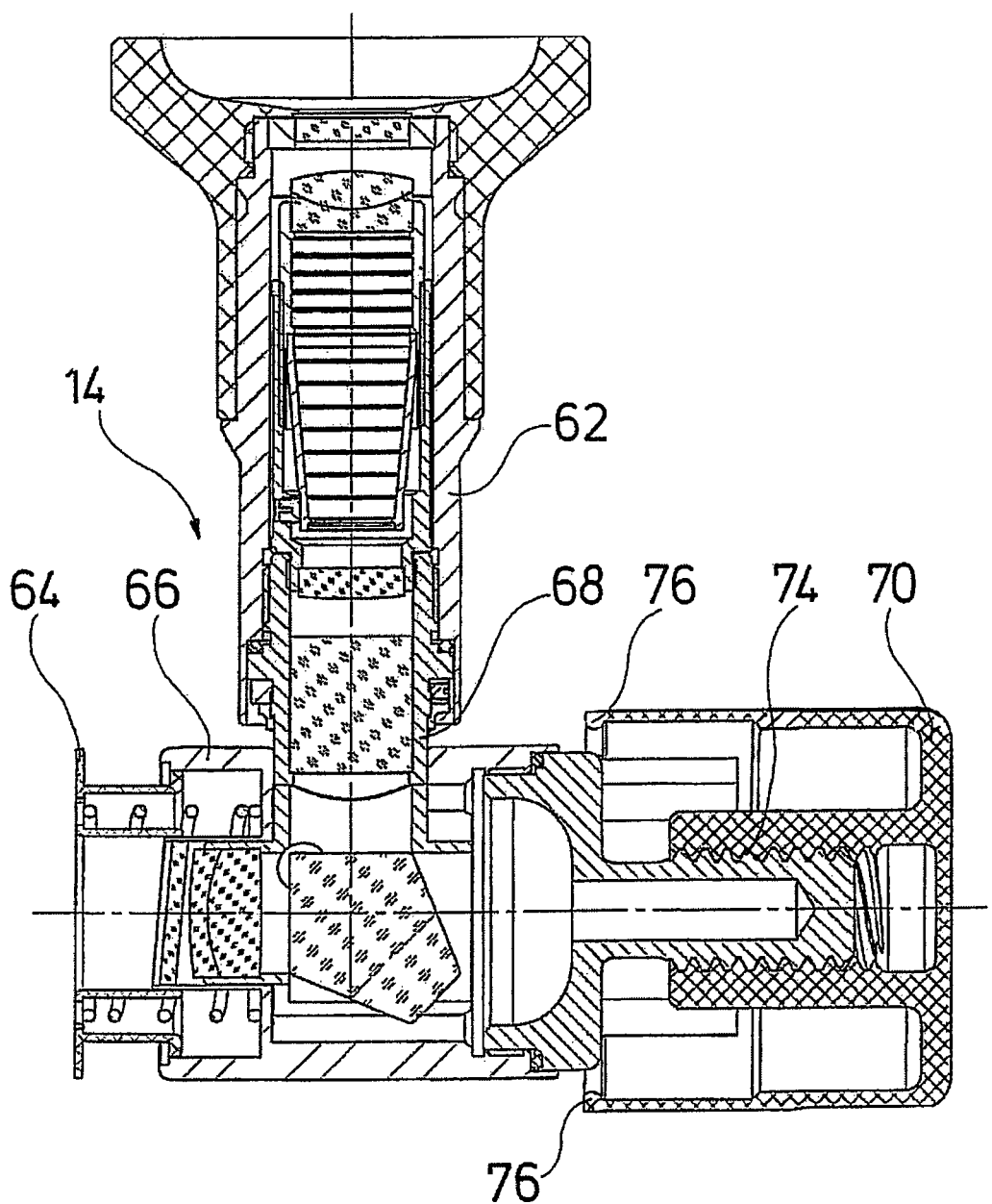
FIG. 7 is a sectional view of the removable ocular according to FIG. 6.
Figure 8:
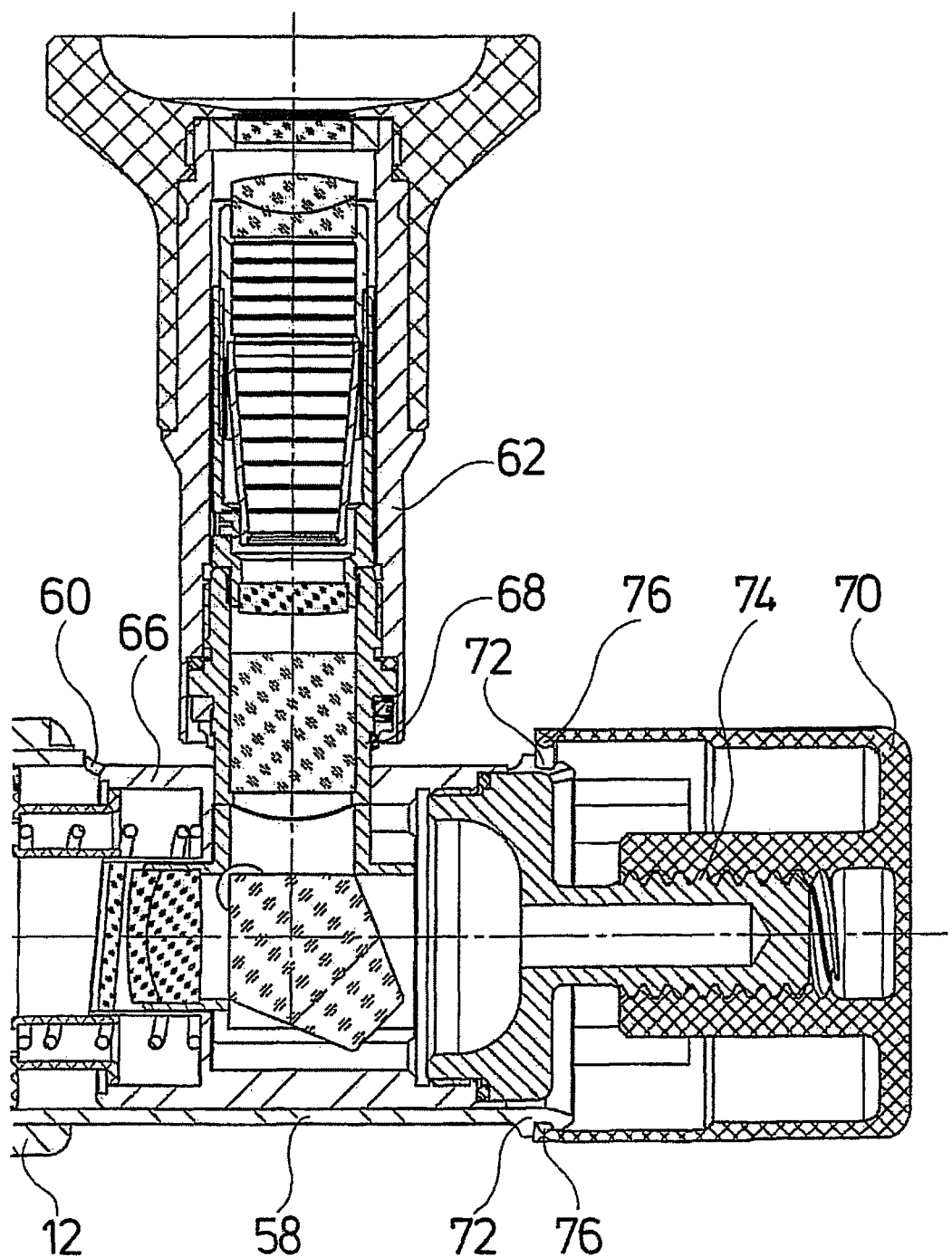
FIG. 8 is a sectional view of the ocular according to FIG. 6, in the installed condition.

The ocular 14 is displaceably arranged on the component 58 of the observation device 12. For this, the component 58 at its end which is distanced to the ocular 16, comprises a sleeve 58 which is open to the outside and which is provided with a longitudinal slot 60 which is open to the outside. As can be deduced from FIG. 6, the ocular 14 comprises two ocular parts 62 and 66 which are aligned perpendicularly to one another, wherein the ocular part 62 serving for observation is fastened on the sleeve 66. A light protection sleeve 64 is displaceably mounted in the ocular part 66. The ocular 14 is insertable with the sleeve 66 into the sleeve 58 of the observation device 12, wherein a tapering 68 formed on the ocular part 62 engages into the longitudinal slot 60. At one end, the ocular 14 comprises a fastening part 70 with an inner thread 74, which is formed therein and which for fastening the ocular 14 on the sleeve 58 of the observation device 12, is connected to a positive fit 72 provided there, via an annular shoulder 76.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A stereo-endoscope comprising a hollow shank (2), two axially parallel optical channels (22, 24) which run through the hollow shank (2), each of the optical channels respectively forming at least a section of an image path to one of two oculars (14, 16) of a binocular observation device (12) arranged on a proximal end of the hollow shank (2), a camera connection (10), a first one of the optical channels also forming at least one section of an image path to the camera connection (10), a beam splitter (42, 46) comprising a deflection prism (42) and a glass component (46), the beam splitter being arranged on a proximal end of the first optical channel (22) between one of the two oculars (14, 16) and an axial end side of the first optical channel (22) closest to the one of the two oculars (14, 16) and optically connecting the first optical channel (22) to one of the oculars (16) and to the camera connection (10), and means for reducing image brightness arranged on a proximal end of a second (24) of the optical channels between the other of the two oculars (14, 16) and an axial end side of the second optical channel (24) closest to the other of the two oculars (14, 16).

2. The stereo-endoscope according to claim 1, wherein respective longitudinal axes (B, C) of the optical channels (22, 24) are arranged in a common plane with a longitudinal axis (A) of the hollow shank (2).

3. The stereo-endoscope according to claim 1, wherein the means for reducing image brightness comprises a glass component (56) arranged on the proximal end of the second optical channel (24), and a coating on the glass component.

4. The stereo-endoscope according to claim 1, wherein an image path leading from the first optical channel (22) to the ocular (16), and the image path leading from the first optical channel (22) to the camera connection (10), are angled to one another.

5. The stereo-endoscope according to claim 1, wherein image paths leading at a proximal end from the optical channels (22, 24) to the binocular observation device are aligned angled to the optical channels (22, 24).

6. The stereo-endoscope according to claim 1, wherein the binocular observation device (12) comprises a stationary ocular (16) and an ocular (14) which is displaceable in a longitudinal direction.

7. The stereo-endoscope according to claim 6, wherein the observation device comprises a sleeve (58) directed normally to longitudinal axes of the oculars (14, 16), and wherein the displaceable ocular (14) is guided displaceably in a longitudinal slot (60) on the sleeve (58).

8. The stereo-endoscope according to claim 6, wherein the displaceable ocular (14) is releasably fastened on the observation device (12).

9. The stereo-endoscope according to claim 1, wherein optical systems of the stereo-endoscope are closed to be gas-tight.

10. A stereo-endoscope comprising a hollow shank (2), two axially parallel optical channels (22, 24) having equally large cross sections and running through the hollow shank (2), each of the optical channels respectively forming at least a section of an image path to one of two oculars (14, 16) of a binocular observation device (12) arranged on a proximal end of the hollow shank (2), a camera connection (10), a first one of the optical channels also forming at least one section of an image path to the camera connection (10), a beam splitter (42, 46) arranged on a proximal end of the first optical channel (22) and optically connecting the first optical channel (22) to one of the oculars (16) and to the camera connection (10), and means for reducing image brightness arranged on a proximal end of a second (24) of the optical channels.

* * * * *